United States Patent
Saunders

(10) Patent No.: US 6,468,240 B1
(45) Date of Patent: *Oct. 22, 2002

(54) SELF-SEATING OCCIPUT WEDGE SYSTEM FOR APPLYING A THERAPEUTIC TRACTION FORCE

(75) Inventor: H. Duane Saunders, Eden Prairie, MN (US)

(73) Assignee: The Saunders Group, Inc., Chaska, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/756,100

(22) Filed: Jan. 8, 2001

Related U.S. Application Data

(63) Continuation of application No. 09/369,921, filed on Aug. 6, 1999, now Pat. No. 6,171,273.

(51) Int. Cl.⁷ .................................................. A61F 5/00
(52) U.S. Cl. .......................................... 602/38; 602/32
(58) Field of Search .............................. 602/32, 33, 35, 602/36, 38, 40; 606/237, 240, 242, 201; 601/23, 39; 5/636, 637, 640, 642; 128/869–870, 875

(56) References Cited

U.S. PATENT DOCUMENTS

| | | |
|---|---|---|
| 738,283 A | 9/1903 | Blomqvist |
| 1,205,649 A | 11/1916 | Miller |
| 1,242,688 A | 10/1917 | Hawley |
| 1,301,276 A | 4/1919 | Kroetz |
| 1,803,556 A | 5/1931 | Nugent |
| 1,984,520 A | 12/1934 | Curtis |
| 2,166,229 A | 7/1939 | Anderson |
| 2,273,088 A | 2/1942 | Byers |
| 2,534,587 A | 2/1950 | Fisher et al. |
| 2,554,337 A | 5/1951 | Lampert |
| 2,689,127 A | 9/1954 | Silverton et al. |
| 2,723,663 A | 11/1955 | Davis |
| 2,733,712 A | 2/1956 | Wuesthoff |
| 2,831,482 A | 4/1958 | Cobb |

(List continued on next page.)

FOREIGN PATENT DOCUMENTS

| | | |
|---|---|---|
| DE | 716904 | 10/1954 |
| DE | 2207847 | 8/1973 |
| DE | 2622255 | 11/1977 |
| FR | 997691 | 1/1952 |
| FR | 2388548 | 12/1978 |
| GB | 2038185 | 7/1980 |
| WO | WO 96/14810 | 5/1996 |

OTHER PUBLICATIONS

Glacier Cross, Inc. product brochure, PRONEX™, "A patient–controlled pneumatic device for the comfortable and secure management of cervical pain," 1 p. (undated).

Zinco Industries, Inc. product brochure, Pneu–trac™, Air Pressure the Patient Controls, 1 p. (undated).

"Spinal Traction," *Evaluation, Treatment and Prevention of Musculoskeletal Disorders*, Chapter 10, pp. 275–302 (updated).

Primary Examiner—Justine R. Yu
(74) Attorney, Agent, or Firm—Faegre & Benson LLP

(57) ABSTRACT

A self-seating occiput wedge system for applying a therapeutic traction force to the occipital areas on a patent's head. The self-seating occiput wedge system includes a pair of self-seating, upstanding occiput wedges rotatably mounted generally perpendicular to a carriage. The occiput wedges define opposing engaging surfaces arranged to engage with the occipital areas of the patient's head. End stops define a range of rotation about an axis of rotation for each of the occiput wedges. The range of rotation is about 20 degrees. A cervical traction device utilizes the occiput wedge system is also disclosed.

19 Claims, 7 Drawing Sheets

U.S. PATENT DOCUMENTS

| | | | |
|---|---|---|---|
| 2,910,061 A | 10/1959 | Rabjohn |
| 2,966,906 A | 1/1961 | Wiltrout |
| 3,060,925 A | 10/1962 | Honsaker et al. |
| 3,176,684 A | 4/1965 | Walsh |
| 3,293,667 A | 12/1966 | Ohrberg |
| 3,336,922 A | 8/1967 | Taylor |
| 3,387,605 A | 6/1968 | Schmidt |
| 3,413,971 A | 12/1968 | Evans |
| 3,522,802 A | 8/1970 | Morton |
| 3,548,817 A | 12/1970 | Mittasch |
| 3,554,189 A | 1/1971 | Hendrickson |
| 3,561,434 A | 2/1971 | Kilbey |
| 3,596,655 A | 8/1971 | Corcoran |
| 3,621,839 A | 11/1971 | Barthe |
| 3,675,646 A | 7/1972 | Cororan |
| 3,827,429 A | 8/1974 | Heikes |
| 3,828,377 A | 8/1974 | Fary, Sr. |
| 3,847,146 A | 11/1974 | Cushman |
| 3,888,243 A | 6/1975 | Powlan |
| 3,937,216 A | 2/1976 | Brown |
| 3,957,040 A | 5/1976 | Calabrese |
| 4,146,021 A | 3/1979 | Brosseau et al. |
| 4,146,612 A | 3/1979 | Veber |
| 4,154,478 A | 5/1979 | Cohune |
| 4,166,459 A | 9/1979 | Nightingale |
| 4,242,946 A | 1/1981 | Toliusis |
| 4,320,749 A | 3/1982 | Highley |
| 4,356,816 A | 11/1982 | Granberg |
| 4,428,276 A | 1/1984 | Loveless |
| 4,436,303 A | 3/1984 | McKillip et al. |
| 4,466,427 A | 8/1984 | Granberg |
| 4,545,572 A | 10/1985 | Day |
| 4,583,532 A | 4/1986 | Jones |
| 4,649,907 A | 3/1987 | Whitehead et al. |
| 4,664,101 A | 5/1987 | Granberg |
| 4,669,455 A | 6/1987 | Bellati |
| 4,736,736 A | 4/1988 | Moers et al. |
| 4,760,842 A | 8/1988 | Holmes |
| 4,771,493 A | 9/1988 | Park |
| RE32,791 E | 11/1988 | Saunders |
| 4,805,603 A | 2/1989 | Cumberland |
| 4,832,007 A | 5/1989 | Davis, Jr. et al. |
| 4,951,654 A | 8/1990 | Gambale et al. |
| 4,981,034 A | 1/1991 | Haeg |
| 4,981,148 A | 1/1991 | Fuller |
| 4,991,572 A | 2/1991 | Chases |
| 4,995,378 A | 2/1991 | Dyer et al. |
| 5,052,378 A | 10/1991 | Chitwood |
| 5,067,483 A | 11/1991 | Freed |
| 5,092,322 A | 3/1992 | Gantz |
| 5,154,186 A | * 10/1992 | Laurin et al. ............... 128/870 |
| 5,169,160 A | 12/1992 | Gaskill et al. |
| 5,181,904 A | 1/1993 | Cook et al. |
| 5,265,625 A | 11/1993 | Bodman |
| 5,360,392 A | 11/1994 | McCoy |
| 5,382,226 A | 1/1995 | Graham |
| 5,441,479 A | 8/1995 | Chitwood |
| 5,454,781 A | 10/1995 | Chitwood |
| 5,569,175 A | 10/1996 | Chitwood |
| 5,653,678 A | 8/1997 | Fulk |
| 5,662,597 A | 9/1997 | Chitwood |
| 5,709,649 A | 1/1998 | Chitwood |
| 5,722,941 A | 3/1998 | Hart |
| 5,868,471 A | * 2/1999 | Graham et al. ............. 297/397 |
| 5,957,876 A | 9/1999 | D'Amico |
| 6,059,548 A | 5/2000 | Cambell et al. |
| 6,305,749 B1 | * 10/2001 | O'Connor et al. .......... 297/397 |

* cited by examiner

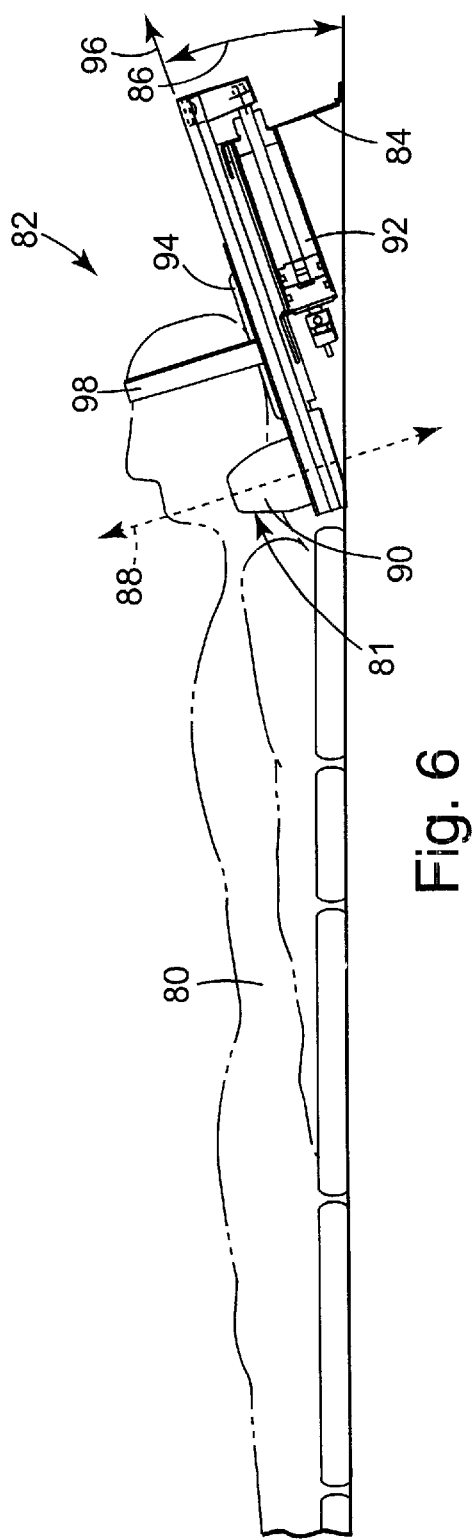
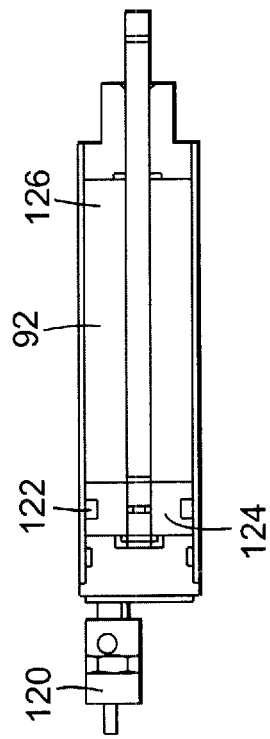

SELF-SEATING OCCIPUT WEDGE SYSTEM FOR APPLYING A THERAPEUTIC TRACTION FORCE

The present application is a continuation of U.S. application Ser. No. 09/369,921, filed Aug. 6, 1999, now U.S. Pat. No. 6,171,273.

FIELD OF THE INVENTION

The present invention is directed to a self-seating occiput wedge system for applying a therapeutic traction force to the occipital areas on a patent's head and neck, and to a cervical traction device utilizing the occiput wedge system.

BACKGROUND OF THE INVENTION

Traction is widely used to relieve pressure on inflamed or enlarged nerves. While traction is applicable to any part of the body, cervical and lumbar or spinal traction are the most common. When correctly performed, spinal traction can cause distraction or separation of the vertebral bodies, a combination of distraction and gliding of the facet joints, tensing of the ligamentous structures of the spinal segment, widening of the intervertebral foramen, straightening of spinal curvature and stretching of the spinal musculature. Depending on the disorder being treated, the traction component of physical therapy may require multiple sessions per week for a prolonged period of time.

U.S. Pat. No. RE 32,791 (Saunders) discloses a cervical traction device that includes a pair of v-shaped adjustable arms that grip the rear area of the patients head approximate the occipital bone and mastoid processes. The lateral separation between the v-shaped arms is adjustable to fit various size patients. The v-shaped arms grip the rear of the patient's head while leaving the mouth and jaw of the patient unrestricted. The cervical traction device of RE 32,791 is utilized on a conventional traction table, presumably under the care of a physician or a physical therapist. It is the physical therapist or other healthcare provider that adjusts the lateral separation of the v-shaped arms to fit the patient and correctly positions the patient relative to the cervical traction device.

With the advent of portable and in-home traction devices, patients perform traction therapy without the direct supervision of a healthcare provider. A low cost portable cervical traction device powered by a pneumatic cylinder that utilizing v-shaped adjustable arms generally disclosed in RE 32,791 is disclosed in WO 96/14810 (Saunders). The lateral position of the v-shaped neck supports is adjusted by the patient by turning left and right knobs coupled to a threaded shaft.

For portable or in-home traction devices to be safe and effective, the patient must properly adjust the lateral separation of the v-shaped neck supports and properly position his/her body relative to the cervical traction device. Moreover, since the shape of the occipital region varies from patient to patient, even properly adjusted neck supports can create uncomfortable locations of high pressure on the patients occipital region. Additionally, the lateral adjustment mechanism for the v-shaped neck supports adds considerable costs to the overall traction device. Consequently, what is needed is a self-seating occiput wedge system for cervical traction devices that also eliminates the cost of a mechanism for adjusting the lateral separation between the occiput wedges.

BRIEF SUMMARY OF THE INVENTION

The present invention is directed to a self-seating occiput wedge system for applying a therapeutic traction force to the occipital areas on a patent's head. Since the size and shape of the occipital region of patients can vary considerably, the occiput wedges rotate independently to present occipital regions of various shapes with the largest available engaging surface, thereby increasing comfort and therapeutic effectiveness. The present occiput wedge system may be combined or used with various cervical traction devices.

The self-seating occiput wedge system is configured to apply a therapeutic traction force to occipital areas on a patient's head in the cervical traction device. The cervical traction device includes a carriage slidable along a portion of a supporting track parallel to a longitudinal axis and a traction force generator engagable with the carriage. The self-seating occiput wedge system includes a pair of upstanding occiput wedges rotatably mounted generally perpendicular to the carriage. The occiput wedges define opposing engaging surfaces arranged to engage with the occipital areas of the patient's head. End stops define a range of rotation about an axis of rotation for each of the occiput wedges. The range of rotation is typically about 20 degrees. In alternate embodiments, the range of rotation may be about 10 degrees to about 30 degrees.

In one embodiment, each of the occiput wedges rotate independently. In an alternate embodiment, the rotation of the occiput wedges may be mechanically coupled.

The engaging surfaces typically have a concave contour. The engaging surfaces may be asymmetrical with respect to the axis of rotation. The engaging surfaces have a radius of curvature in a plane perpendicular to the axis of rotation of about 10.85 centimeters (4.27 inches). The engaging surfaces have a radius of curvature in a plane containing the axis of rotation of about 6.66 centimeter (2.62 inches). The occiput wedge system may optionally include a head support pad.

The present invention is also directed to a cervical traction device including the present self-seating occiput wedge system. The cervical traction device may be a stand-alone device with its own traction force generator or an accessory that can be used with a traction table and the traction force generator associated with the table.

The cervical traction device typically includes a carriage slidable along a portion of a supporting track parallel to a longitudinal axis. A traction force generator moves the carriage along the supporting track. The supporting track and carriage may be portions of a traction table, such as the segmented traction table illustrated herein. The traction force generator may be a pneumatic or a hydraulic cylinder, an electric motor, a spring-loaded device, or the like. In one embodiment, the traction force generator comprises a pneumatic cylinder attached to a support structure for moving the carriage relative to the support structure when in a pressurized state and a hand pump fluidly connected to the pneumatic cylinder for injecting pressurized air into the pneumatic cylinder.

BRIEF DESCRIPTION OF THE SEVERAL VIEWS OF THE DRAWING

FIG. 6 is a schematic illustration of a cervical traction device utilizing the self-seating occiput wedge system of the present invention.

FIG. 7 illustrates a pneumatic cylinder for use with the present cervical traction device.

DETAILED DESCRIPTION OF THE INVENTION

Figure 1:
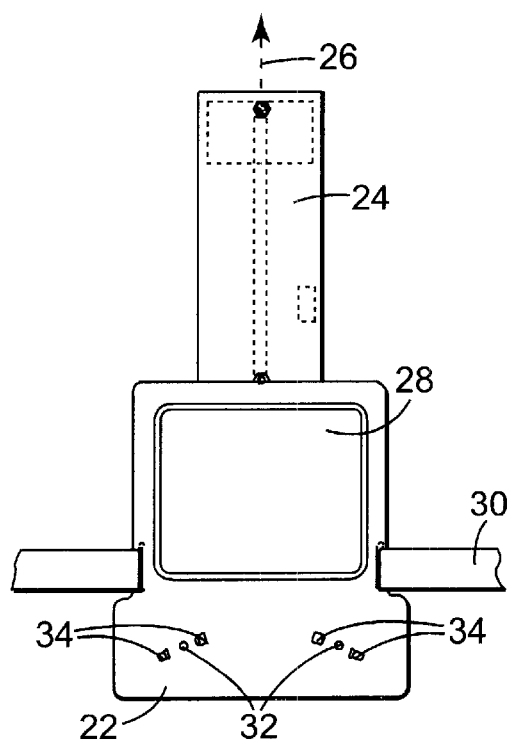
FIG. 1 is a top perspective view of a sliding carriage for use in a cervical traction device in accordance with the present invention.

FIGS. 1–5 illustrate various components of a self-seating occiput wedge system 20 in accordance with the present invention. FIG. 1 illustrates a carriage 22 slidable along a support track 24 parallel to a longitudinal axis 26. The carriage 22 optionally includes the head support pad 28 and a head strap 30. The carriage 22 includes a pair of mounting holes 32 arranged along a line perpendicular to the longitudinal axis 26. Adjacent to each of the mounting holes 32 is a pair of end stops 34.

Figure 2:
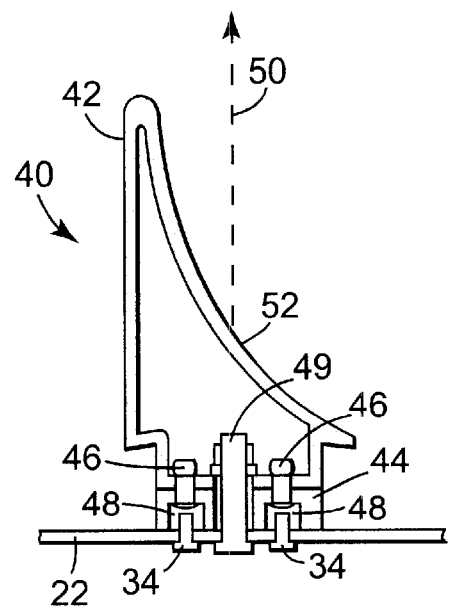
FIG. 2 is side sectional view of an occiput wedge support assembly in accordance with the present invention.

FIG. 2 is a side sectional view of an occiput wedge support assembly 40 rotatable mounted to the carriage 22. The occiput wedge support assembly 40 includes an occiput wedge support 42 attached to a spacer block 44 by a pair of fasteners 46. In the illustrated embodiment, the occiput wedge support 42 is an aluminum extrusion having a concave engaging surface 52 located in a plane including the axis of rotation 50 and a generally planar surface in a plane perpendicular to the axis of rotation 50. The spacer block 44 includes a pair of end stops receiving holes 48 that have a diameter or cross-section greater than the diameter or cross-section of the end stops 34.

The occiput wedge support assembly 40 is mounted to the carriage 22 by a fastener 49 extending through the mounting hole 32. The end stops 34 can be threaded fasteners, rivets, portions of the carriage 22 stamped to form an upright structure, or a variety of other structures. Neither the end stops 34 nor the end stop receiving holes 48 need to have a circular cross-section.

The combination of the mounting hole 32 and the fastener 46 define an axis of rotation 50 about which the occiput wedge support assembly 40 can rotate. Since the diameter of the end stops 34 is smaller than the diameter of the end stop receiving holes 48, the entire occiput wedge support assembly 40 can rotate about the axis rotation 50 until the end stops 34 engage with an inside edge of an end stop receiving hole 48. The range of rotation is typically about 20 degrees, but may be about 10 degrees to about 30 degrees in other embodiments. A single end stop 34 may be used with each of the occiput wedge support assemblies 40. Moreover, a variety of other end stop mechanisms are possible for achieving this function.

Figure 3:
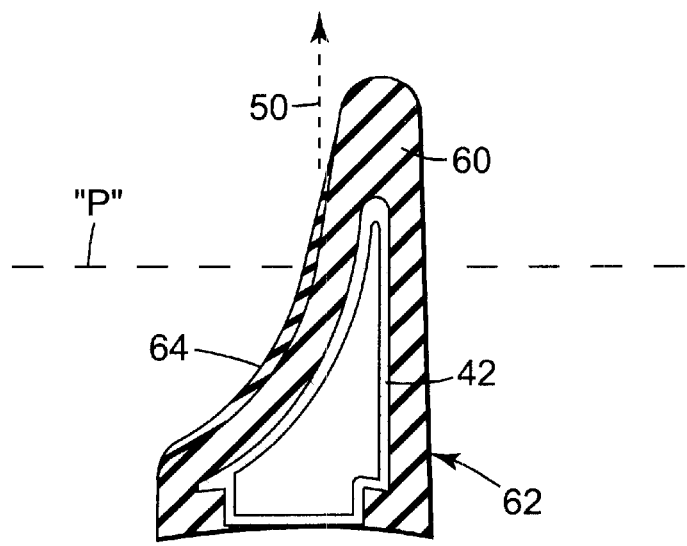
FIG. 3 is a perspective view of an occiput wedge in accordance with the present invention.
Figure 4:
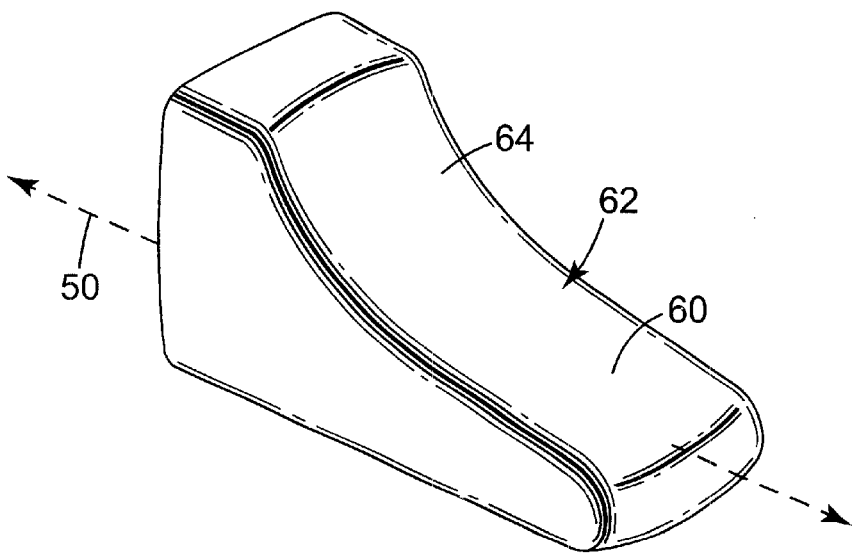
FIG. 4 is a side sectional view of the occiput wedge of FIG. 3.

FIG. 3 is a side sectional view of the occiput wedge 62 including an elastomeric covering 60 extending over the occiput wedge support 42. The elastomeric covering can be constructed from a variety of materials, including without limitation ethylene propylene diene monomer (EPDM) flexible resilient foam. The elastomeric covering 60 has a concave engaging surface 64 that generally follows the contour of the concave surface 52 on the occiput wedge support 42. The thickness of the elastomeric cover 60 between the engaging surface 64 and the concave surface 52 is generally about 19 millimeters (0.75 inches). The engaging surface 64 has a radius of curvature in plane containing the axis rotation 50 of about 6.66 centimeters (2.62 inches).

On the other hand, the concave surface 64 has a radius of curvature in a plane perpendicular to the axis of rotation 50 of about 10.85 centimeters (4.27 inches). That is, in a plane perpendicular to the axis of rotation 50, the engaging surface 64 has minimal curvature through the range of rotation 74 (see FIG. 5). The fairly flat engaging surface 64 in the plane perpendicular to the axis of rotation 50 is intended to minimize sharp or abrupt transition points along the occiput wedge 62 that can concentrate pressure on the occipital area of the patient's head.

Figure 5:
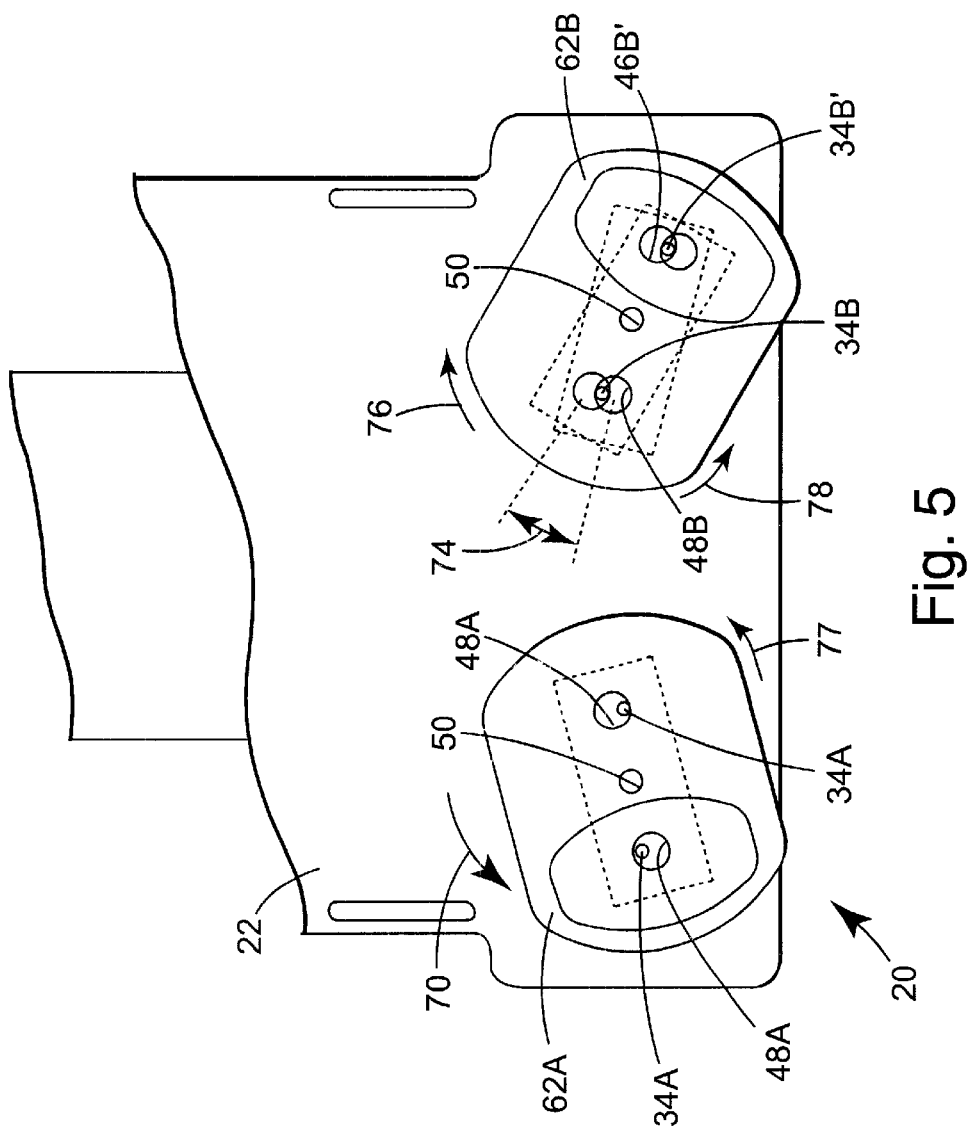
FIG. 5 is a top sectional view of an occiput wedge system in accordance with the present invention.

FIG. 5 is a top perspective view of a self-seating occiput wedge system 20 in accordance with the present invention. The occiput wedges 62A, 62B are rotatably mounted to the carriage 22 about an axis of rotation 50. With regard to the occiput wedge 62A, the end stops 34A are engaged with opposite edges of the end stop receiving holes 48A. As illustrated in FIG. 5, the occiput wedge 62A is fully rotated in the direction 70.

With regard to the occiput wedge 62B, the occiput wedge support 42B is shown in phantom at the opposite extremes of the range of rotation 74. When the occiput wedge 62B is rotated to the extreme in the direction 76, the end stop 34B is engaged with the bottom of the end stop receiving hole 48B and the end stop 34B' is engaged with the top of the end stop receiving hole 48B'. When the occiput wedge 62B is rotated to the extreme in the direction 78, the end stop 34B is engaged with the top of the end stop receiving hole 48B and the end stop 34B' is engaged with the bottom of the end stop receiving hole 48B'.

The lateral separation between the axes of rotation 50 of the occiput wedges 62A, 62B is not adjustable, but rather, is fixed based upon experimental analysis at about 10 centimeters. In an alternate embodiment, the lateral separation between the axes of rotation 50 can be fixed at a distance of about 9.5 centimeters to about 11.5 centimeters. The actual functional distance between the opposing occiput wedges 62A, 62B depends upon the shape of the engaging surfaces 64 and the location on the concave engaging surface 64 where the patient positions his/her head. For example, a patient with a small head and neck will engage the occiput wedges 62A, 62B closer to the head support pad 28 than a patient with a larger head and neck. Therefore, it is possible for a patient to engage his/her head with the occiput wedges 62A, 62B without touching the head support pad 28

In operation, the patient positions his/her head and neck between the occiput wedges 62A, 62B. The occiput wedges 62A, 62B rotate independently in either direction 70, 77 and 76, 78, respectively, so that the maximum surface area of the engaging surface 64 is seated against the patient's head and neck. The rotation of the occiput wedges 62A, 62B is intended primarily to comfortably seat the engaging surfaces 64 with the patient's head and neck. Locations of high pressure at the interface of the patient's occipital region and the engaging surfaces 64 provide a moving force that rotates the occiput wedges 62A, 62B to create a more uniform pressure distribution on the occipital bone of the patient. The independent rotation of the occiput wedges 62A, 62B compensates for asymmetry in the shape of the patient's occipital region and general misalignment of the patient relative to the occiput wedge system 20.

As the traction force is applied, the occiput wedges 62A, 62B tend to rotate slightly so that the maximum, most comfortable, surface area of the engaging surfaces 64 is seated against the head and neck of the patient. The low curvature of the engaging surfaces 64 along a plane perpendicular to the axis of rotation 50 and the relatively small range of rotation 74 minimize rotation after the occiput wedges 65A, 62B are seated.

FIG. 6 is a schematic illustration of a patient 80 engaged with a cervical traction device 82 utilizing the occiput wedge system 81 of the present invention. Support arm 84 holds the cervical traction device 82 at the desired flexion angle 86. The axes of rotation 88 of the occiput wedges 90 are offset from perpendicular by approximately the flexion angle 86. Pneumatic cylinder 92 provides a traction force that moves the carriage 94 along a longitudinal axis 96. In the illustrated embodiment, headband 98 is provided for retaining the patient's head and neck to the cervical traction device 82.

FIG. 7 illustrates a single-acting pneumatic cylinder 92 suitable for use in the cervical traction device 82 of FIG. 6. The pneumatic cylinder 92 includes at least one pressure regulator 120 to prevent the pressure in the pneumatic cylinder 92 from exceeding a predetermined value. The pneumatic cylinder 92 includes at least one pressure activated seal 122 arranged circumferentially around a piston 124. The pressure-activated seal is a generally V-shaped seal member arranged to expand when the air pressure in the pneumatic cylinder 92 exceeds about 13.8 kPa (2 psi). The pneumatic cylinder 92 is capable of maintaining a generally static traction force of greater than 111 N (25 pounds) for a period in excess of 10 minutes without additional pressurized air being injected into the cylinder 126. A pneumatic cylinder suitable for use in the cervical traction device 82 is disclosed in U.S. patent application Ser. No. 08/817,444, entitled Portable Traction Device.

Figure 8:
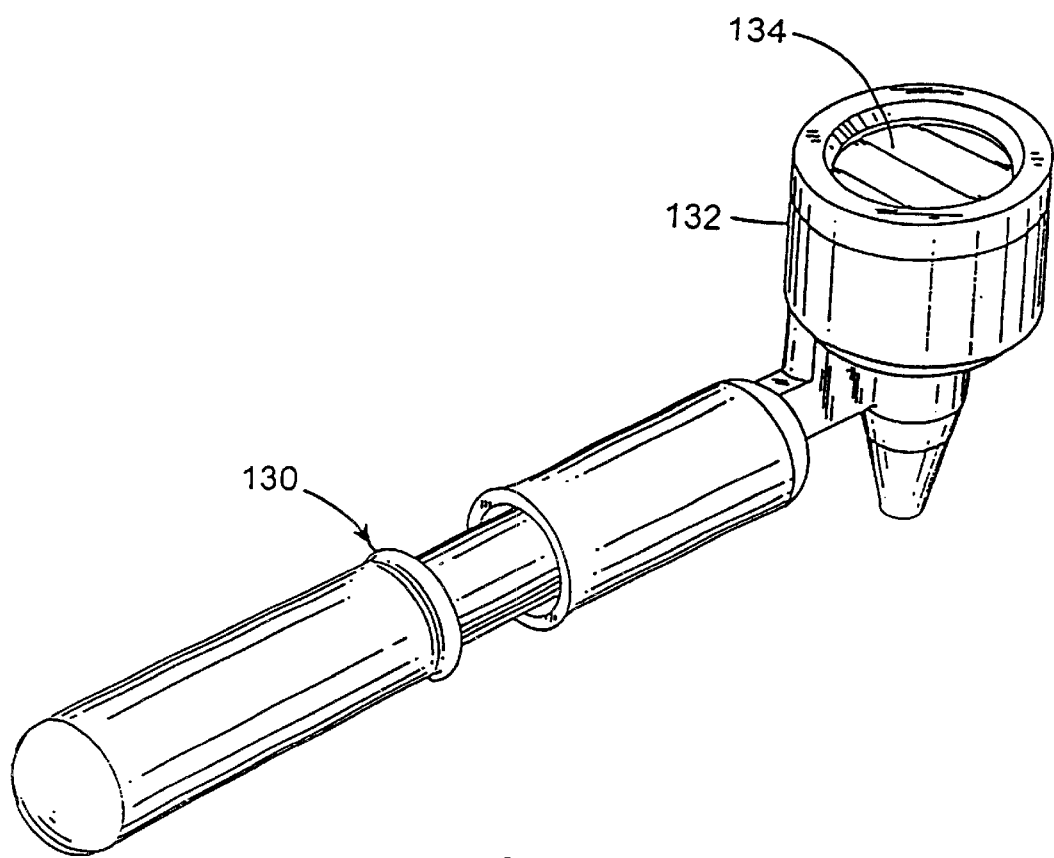
FIG. 8 illustrates a hand pump for use with the present cervical traction device.

FIG. 8 is a perspective view of a hand pump 130 suitable for activating the pneumatic cylinder 92. The hand pump 130 includes a valve 132 to manually release pressure in the pneumatic cylinder 92, and a gauge 134 to indicate the traction force being applied. A suitable hand pump is disclosed in U.S. patent application Ser. No. 09/092,451, entitled Hand Pump System for a Traction Device.

Figure 9:
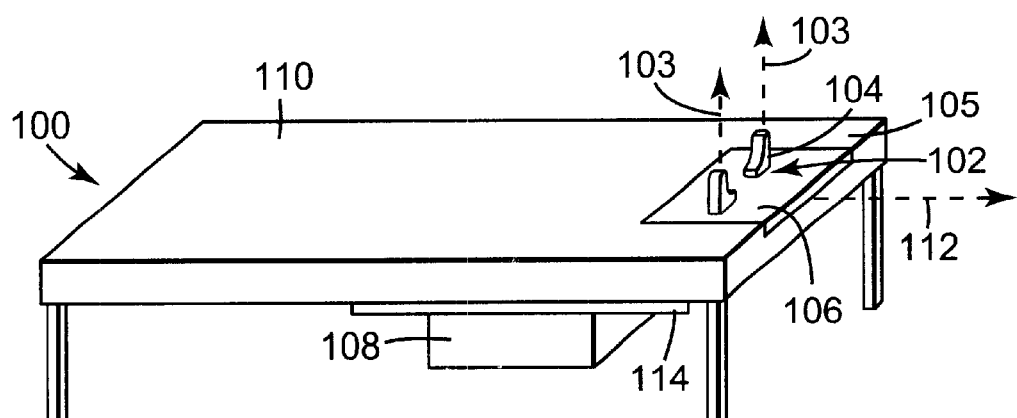
FIG. 9 is a perspective view of a traction table utilizing the self-seating occiput wedge system of the present invention.

FIG. 9 is a schematic illustration of a segmented traction table 100 utilizing a self-seating occiput wedge system 102 in accordance with the present invention. In the illustrated embodiment, a pair of opposing occiput wedges 104 rotatably mounted to a carriage 106 on the upper portion 105 of the traction table 100. Axes of rotation 103 are generally perpendicular to the carriage 106. The occiput wedges 104 can optionally be removable from the traction table 100 to permit other traction therapies.

In the illustrated embodiment, a traction device 108 is provided for moving the carriage 106 relative to a lower portion 110 along a supporting track 114 parallel to axis 112. The carriage 106 and the occiput wedges 104 are simultaneously moved along the axis 112 to provide a traction force to a patient (not shown). Friction between the patient's body and the lower portion 110 is typically sufficient to provide a counter force for the cervical traction procedure. Alternatively, various belts and straps can be utilized on the lower portion 110 of the traction table 100 to retain the patient thereto.

Figure 10:
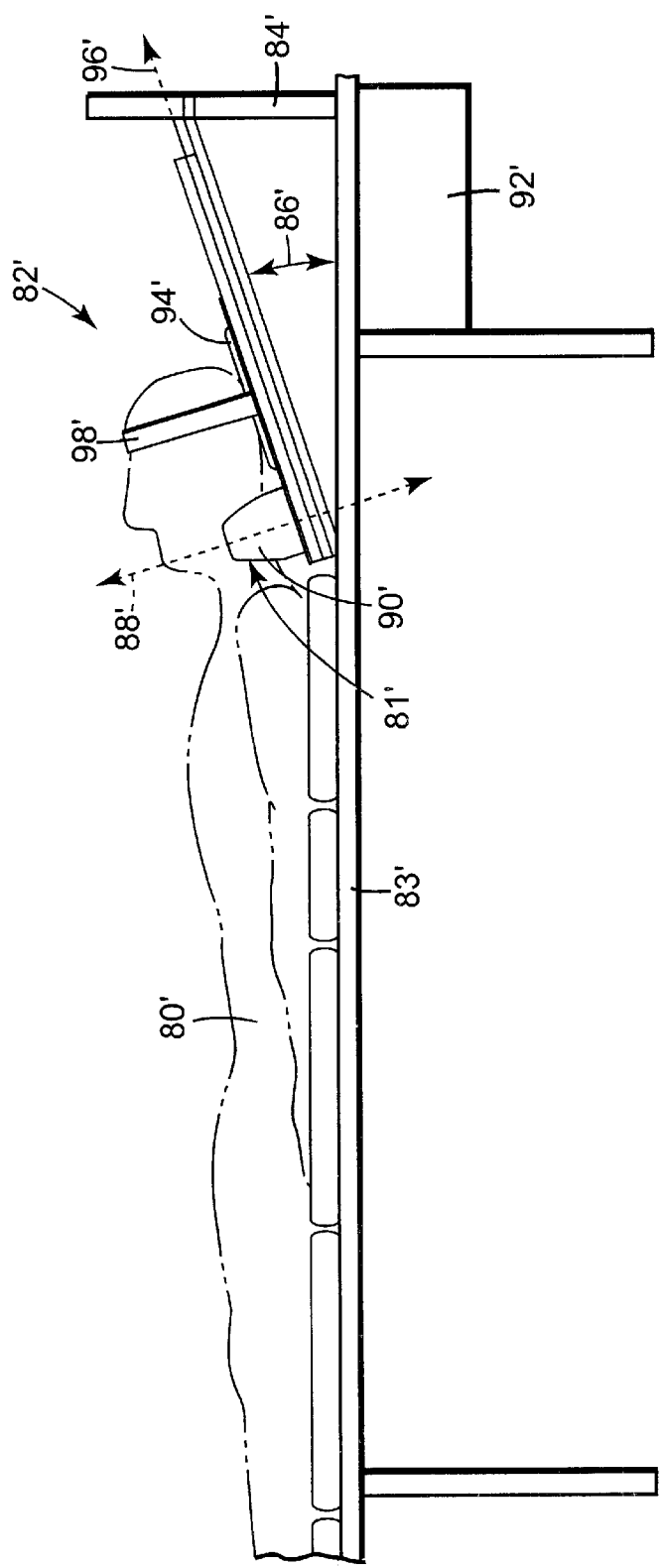
FIG. 10 is a schematic illustration of a cervical traction device utilizing the self-seating occiput wedge system of the present invention on a conventional traction table.

FIG. 10 is a schematic illustration of a patient 80' located on a conventional traction table 83' engaged with a cervical traction device 82' utilizing the occiput wedge system 81' of the present invention. Support arm 84' holds the cervical traction device 82' at the desired flexion angle 86'. The axes of rotation 88' of the occiput wedges 90' are offset from perpendicular by approximately the flexion angle 86'. A traction force generator 92' located on the traction table 83' provides a traction force that moves the carriage 94' along a longitudinal axis 96'. In the illustrated embodiment, headband 98' is provided for retaining the patient's head and neck to the cervical traction device 82'. The cervical traction device 82' can be removed from the traction table 83'

The complete disclosures of all patents, patent applications, and publications are incorporated herein by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A cervical traction device configured to apply a therapeutic traction force to occipital areas on a patient's head, the cervical traction device comprising:
   a carriage slidable along a portion of a supporting track parallel to a longitudinal axis;
   a pair of upstanding, freely rotating, self-seating occiput wedges rotatably mounted generally perpendicular to the carriage, the occiput wedges defining opposing engaging surfaces arranged to engage with the occipital areas of the patient's head;
   end stops defining a range of rotation about an axis of rotation for each of the occiput wedges; and
   a traction force generator engagable with the carriage.

2. The cervical traction device of claim 1 wherein the supporting track and carriage comprise portions of a traction table.

3. The cervical traction device of claim 1 wherein the supporting track and carriage comprise portions of a segmented traction table.

4. The cervical traction device of claim 1 wherein the traction force generator comprises a pneumatic cylinder attached to a support structure for moving a carriage relative to the support structure when in a pressurized state.

5. The cervical traction device of claim 4 wherein the pneumatic cylinder is capable of maintaining a generally static traction force of greater than 111 N (25 pounds) for a period in excess of 10 minutes without additional pressurized air being injected into the cylinder.

6. The cervical traction device of claim 4 wherein the pneumatic cylinder comprises a single-acting pneumatic cylinder.

7. The cervical traction device of claim 4 wherein the pneumatic cylinder includes at least one pressure regulator to prevent the pressure in the pneumatic cylinder from exceeding a predetermined value.

8. The cervical traction device of claim 4 wherein the pneumatic cylinder comprises at least one pressure activated seal arranged circumferentially around a piston.

9. The cervical traction device of claim 4 wherein the at least one pressure activated seal comprises a generally V-shaped seal member arranged to expand when the air pressure in the pneumatic cylinder exceeds 13.8 kPa (2 psi).

10. The cervical traction device of claim 4 comprising a pump including a valve to manually release pressure in the pneumatic cylinder.

11. The cervical traction device of claim 4 comprising a pump further including a gauge indicating traction force.

12. The cervical traction device of claim 1 wherein the traction force generator comprises one of a pneumatic or a hydraulic cylinder, an electric motor, or a spring.

13. The cervical traction device of claim 1 wherein the traction force generator comprises:

a pneumatic cylinder attached to a support structure for moving a carriage relative to the supporting track when in a pressurized state; and a hand pump fluidly coupled to the pneumatic cylinder for injecting pressurized air into the pneumatic cylinder.

14. The cervical traction device of claim 1 wherein the cervical traction device is releasably attachable to a traction table.

15. The cervical traction device of claim 1 wherein the traction force generator is located on a traction table.

16. A cervical traction device configured to apply a therapeutic traction force to occipital areas on a patient's head, the cervical traction device comprising:

a pair of occiput wedges adapted to independently and freely rotate in response to application of a therapeutic traction force, the occiput wedges having separate and generally parallel axes of rotation, the occiput wedges defining opposing engaging surfaces arranged to engage with the occipital areas of the patient's head; and end stops defining a range of rotation about the axis of rotation of each of the occiput wedges; and a traction force generator adapted to displace the occiput wedges.

17. A cervical traction device having a self-seating occiput wedge system configured to apply a therapeutic traction force to occipital areas on a patient's head, the cervical traction device including a carriage slidable along a portion of a supporting track parallel to a longitudinal axis, the cervical traction device comprising:

a pair of upstanding freely rotatable occiput wedges mounted generally perpendicular to the carriage, the occiput wedges defining opposing engaging surfaces arranged to engage with the occipital areas of the patient's head; and end stops defining a range of rotation about an axis of rotation for each of the occiput wedges; and a traction force generator engagable with the carriage.

18. A cervical traction device having a self-seating occiput wedge system configured to apply a therapeutic traction force to occipital areas on a patient's head, the cervical traction device including a carriage slidable along a portion of a supporting track parallel to a longitudinal axis, the cervical traction device comprising:

a pair of upstanding occiput wedges mounted to the carriage and adapted to independently and freely rotate through a range of rotation of about 10 degrees to about 30 degrees in response to application of a therapeutic traction force, the occiput wedges defining opposing engaging surfaces arranged to engage with the occipital areas of the patient's head; and end stops defining the range of rotation about the axis of rotation for each of the occiput wedges; and a traction force generator engagable with the carriage.

19. A cervical traction device having a self-seating occiput wedge system configured to apply a therapeutic traction force to occipital areas on a patient's head, the cervical traction device including a carriage slidable along a portion of a supporting track parallel to a longitudinal axis, the cervical traction device comprising:

a pair of upstanding freely rotatable occiput wedges adapted to rotate through a range of rotation in response to application of a traction force, the occiput wedges defining opposing engaging surfaces arranged to engage with the occipital areas of the patient's head; and end stops defining the range of rotation about an axis of rotation for each of the occiput wedges; and a traction force generator engagable with the carriage.

* * * * *